United States Patent [19]

Fox

[11] Patent Number: 4,921,986

[45] Date of Patent: May 1, 1990

[54] METHOD AND APPARATUS FOR PRODUCING COBALT ACETATE FROM COBALT CHIP

[75] Inventor: Robert Fox, Arab, Ala.

[73] Assignee: Hall Chemical Company, Arab, Ala.

[21] Appl. No.: 139,793

[22] Filed: Dec. 30, 1987

[51] Int. Cl.$^5$ ............................................. C07F 15/06
[52] U.S. Cl. ................................................... 556/149
[58] Field of Search ......................................... 556/149

[56] References Cited

U.S. PATENT DOCUMENTS

| | | | |
|---|---|---|---|
| 2,395,307 | 10/1943 | Weber et al. | 556/149 |
| 2,416,074 | 2/1947 | Weber et al. | 260/414 |
| 3,133,942 | 5/1964 | Hahl | 556/149 |
| 3,288,567 | 11/1966 | Graham | 23/288 |
| 4,263,143 | 4/1981 | Ebner et al. | 210/639 |

OTHER PUBLICATIONS

Ehret, William, *Smith's College Chemistry*, New York; D. Appleton-Century Company, Inc.

*Primary Examiner*—Paul F. Shaver
*Attorney, Agent, or Firm*—Schmeiser, Morelle & Watts

[57] ABSTRACT

Cobalt acetate solution is produced by flowing a circulating oxygen-containing stream of dilute acetic acid solution containing initially about 20% free acid through a bed of cobalt chips and adding dilute acetic acid solution and introducing additional oxygen into the circulating stream in replenishment of those reactants as the dissolution reaction proceeds.

2 Claims, 4 Drawing Sheets

METHOD AND APPARATUS FOR PRODUCING COBALT ACETATE FROM COBALT CHIP

FIELD OF THE INVENTION

The present invention relates generally to the hydrometallurgical art and is more particularly concerned with a novel method of producing cobalt acetate solution from cobalt masses, and with novel apparatus implementing that method.

BACKGROUND OF THE INVENTION

Production of metal salts of organic acids such as carboxylic acids of 1-8 carbon atoms is an old and well-developed technology. The practice of simply contacting metal with an acid or an acid-containing solution has evolved over time into procedures in which promoters or accelerators are employed with the objective of improving acid-metal reactions and consequent metals dissolution. Metals in powder form have generally been used for the same purposes. Thus heretofore there was no way known to match the rate of dissolution of powdered metals with the same metals in massive form such as broken cathodes, chunks and chips so as to avoid the necessity for reducing the metals to powder form.

SUMMARY OF THE INVENTION

By virtue of the present invention based upon the new concepts and discoveries set out below it is now possible to produce cobalt acetate from pieces of broken cathode, chips and the like at a rate comparable to the best achievable through the use of cobalt powders. Further, this result does not entail the use of an accelerator or a promoter or other additive to assist the metal dissolution process or to enhance product quality or yield. Still further, these new results and advantages carry no significant economic penalty as the process can be carried out with low labor costs typical of the chemical industry and with apparatus requiring only limited capital expenditure.

An important discovery underlying the method and apparatus of this invention is that the rate of cobalt dissolution is directly related to oxygen over pressure, which in turn is related to the pressure of the oxygen gas in contact with acetic acid solution in contact with cobalt. Another significant discovery is that the rate of flow of gas-liquid mixture of oxygen and acetic acid solution through a bed of cobalt chips also has an important bearing on the rate of cobalt dissolution. Additional related findings are that temperature is important in respect to metal dissolution rate, particularly that 180° F. is optimum; that acid-metal reaction rate decreases with diminishing cobalt inventory; and that, most surprisingly, decreasing free acid content of the circulating gas-liquid mixture has no significant effect on the the rate of cobalt dissolution.

A novel concept of ours is to embody these discoveries in a process enabling their use in combination for maximum desired effect. That new process or method of this invention, briefly described, comprises the steps of providing a bed of cobalt chips in a closed reactor vessel, establishing a circulating stream of aqueous acetic acid, introducing oxygen gas into the aqueous acid stream and thereby establishing an oxygen gas atmosphere in the vessel, repeatedly flowing the resulting oxygen-containing stream through the cobalt chip bed, and introducing additional oxygen gas into the circulating stream to maintain the pressure of the oxygen atmosphere at a predetermined level. At intervals the liquid phase may be drawn off and replaced with fresh aqueous acetic acid solution in the course of a single run. Thus, in the batch mode of operation a charge of cobalt chips is contacted with two or three fresh acid solutions during a batch run and the cobalt acetate-containing solutions withdrawn at intervals during the batch run are eventually combined and treated for recovery of cobalt values in the form desired. Then at the onset of each batch run, fresh cobalt chips are loaded to bring the bed to the desired depth or level.

Timing of replenishment of the supply of acetic acid solution in the practice of this invention is to a large extent a matter of choice of the operator. Thus the rate of dissolution of the cobalt metal remains constant as acid concentration falls from an initial level of about 20%, for example, to as low as about 0.2%.

The oxygen content of the circulating stream is established and maintained by introducing oxygen gas into the stream and thereby providing an oxygen atmosphere in the closed reactor vessel in which the circulating stream is flowed in contact with the cobalt chip bed. Thus as oxygen in the stream participates in the cobalt dissolution reaction producing by-product water, additional oxygen gas is introduced into the circulating stream as required to maintain the oxygen atmosphere at the desired predetermined superatmospheric level. Since the reaction is continuous, the flow of make-up oxygen gas into the circulating stream is continuous at rate fluctuations matching those of the cobalt dissolution reaction.

As a somewhat less desirable alternative, the present invention process can be run in a manner like autoclave practice so that instead of introducing oxygen gas as described above to establish and maintain the necessary oxygen in the reaction vessel, oxygen gas fills the volume in the vessel above the acid solution. Oxygen is then absorbed in the acetic acid at the gas-liquid interface and consequently is not entrained in the circulating solution in bubble form.

Another new concept of ours is to implement that novel process with apparatus enabling the practice of this invention on any scale of choice at minimum capital and labor costs. That new apparatus, broadly and generally described, comprises an upright elongated reactor vessel having a metal charge-receiving port and a liquid return and overflow port in its upper portion and a liquid discharge port and a drain and fill port in the lower portion thereof. A charge bed-supporting tray is disposed in the lower portion of the reactor vessel above the liquid discharge port and a recirculation conduit outside the reactor vessel communicates with the liquid inlet and discharge ports. Pump means is connected to the conduit for recirculating liquid entering conduit through the liquid discharge port. Oxygenator means including an oxygen gas demand regulator communicates with the conduit for introducing oxygen gas into the conduit to maintain predetermined oxygen gas pressure in the pressure vessel. Additionally, the apparatus includes a top discharge port in the reactor vessel and an accumulator vessel communicating with the reactor vessel through top discharge port to receive gas and liquid rising through the top of the reactor vessel. A pressure relief valve serves to limit gas pressure in the accumulator vessel.

BRIEF DESCRIPTION OF THE DRAWINGS

Those skilled in the art will gain a further and better understanding of this invention from the drawings accompanying and forming a part of this specification in which.

DETAILED DESCRIPTION OF PREFERRED EMBODIMENTS

Figure 1:
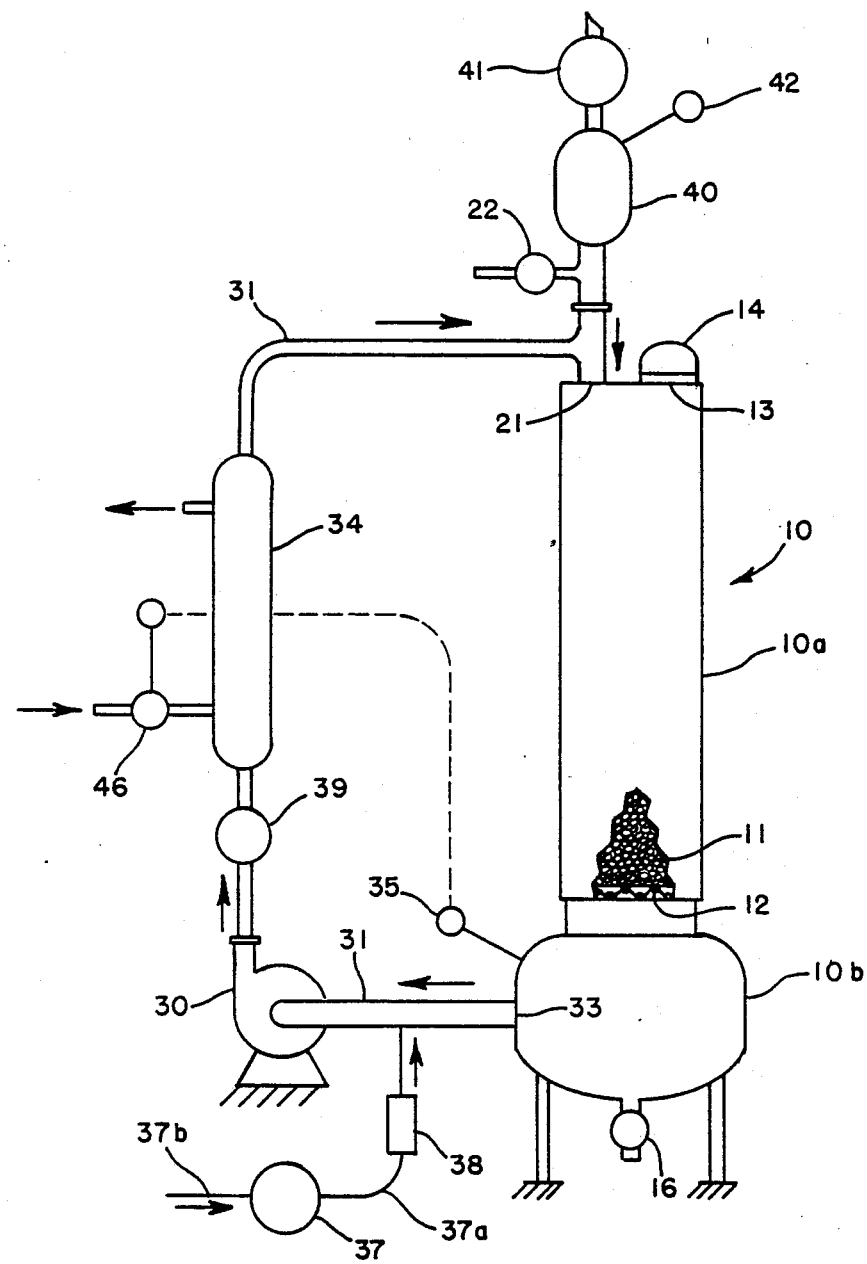
FIG. 1 is an elevational, partially diagrammatic view of apparatus of this invention.

The method of this invention involves flowing a stream of oxygen gas-containing aqueous acetic acid solution in contact with cobalt metal in the form of chips (such as broken pieces of cathode) under conditions resulting in rapid reaction and dissolution of the metal. The gas-liquid stream is recirculated and repeatedly flowed through the bed of cobalt pieces and oxygen gas is introduce-d continuously into the stream. Additionally, for the purpose of achieving maximum dissolution rate the temperature is established and maintained at about 180° F., which represents the best balance between the positive effect of elevated temperature on reaction rate and the negative effect of such temperature on the solubility of oxygen in the acid solution.

In more specific terms the present invention involves charging closed reactor vessel 10 consisting of a column 10a mounted on and opening into a solution reservoir 10b with cobalt chips to provide a chip bed 11 resting on a support grid 12 in the lower part of column 10a. The chips are introduced into the reactor through a metal charge-receiving opening or port 13 in the top of column 10a. Then, after closing opening 13 with hinged closure 14, acetic acid solution is introduced into solution reservoir 10b through drain and fill valve 16 until the liquid level reaches air discharge and fill overflow port 21 and begins to drain to acetic acid solution makeup tank (not shown). Valve 22 serving port 21 and valve 16 are both then closed and recirculation pump 30 serving recirculation conduit 31 is energized to withdraw acetic acid solution from reservoir 10b through outlet port 33 and deliver the solution back into the top of column 10a through port 21 in a continuous recirculation operating mode.

To limit the maximum temperature of the circulating stream which is heated by the exothermic metal dissolution reaction a water jacket 34 is fitted on recirculation conduit 31. Cooling water is delivered into jacket 34 and received therefrom by lines indicated in FIG. 1 and the flow of water through the delivery line is regulated by temperature indicator controller 35 (Foxboro Model 4318) which is operatively connected to a valve 46 in the delivery line and to solution reservoir 10b to sense the temperature of the circulating solution therein.

Figure 4:
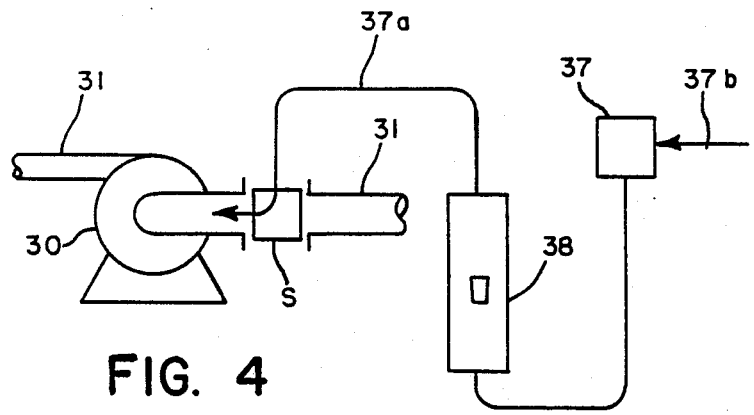
FIG. 4 is a side elevational, partially diagrammatic view the oxygen feed system subassembly of the apparatus of FIG. 1; and, FIG. 5 is a vertical sectional view of the recirculation pump and the suction and discharge portions of the recirculation conduit showing the oxygen feed pipe and spool.
Figure 5:
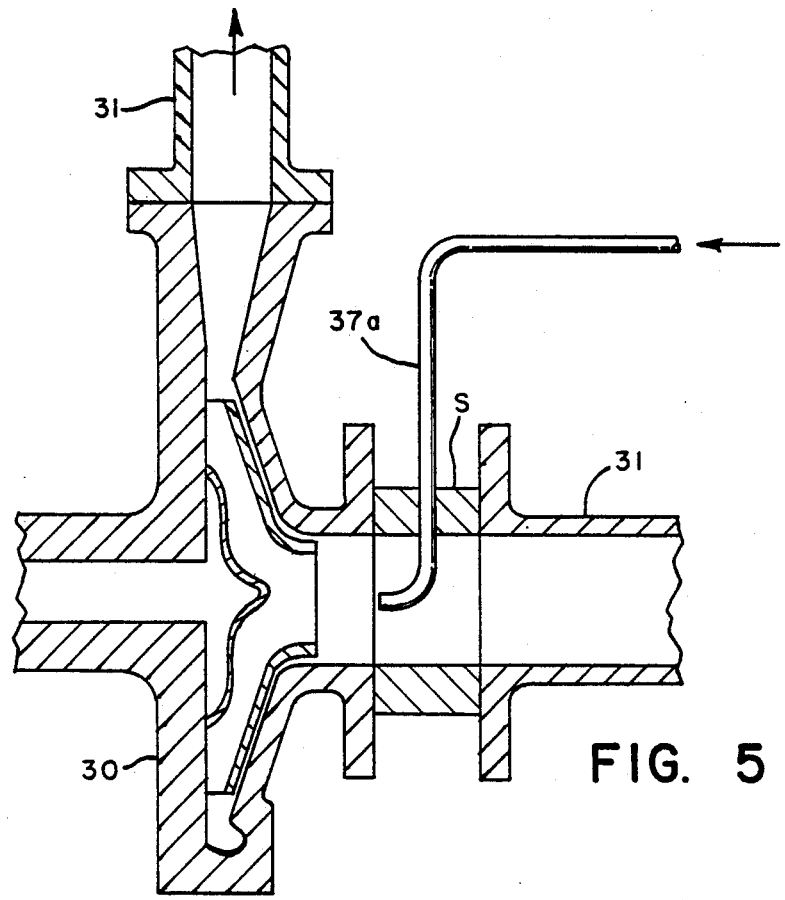

As the chips are dissolved in the acid solution flowing through the chip bed, oxygen is introduced into the recirculating liquid as required to maintain the optimum oxygen pressure level in the system. As shown in FIG. 4, the subassembly serving the essential function comprises a demand regulator 37 (Norgren Regulator No. 11-002-60) controlling oxygen gas input to the acid solution as it flows through conduit 18 from solution reservoir 10b to recirculation pump 30, and a flowmeter 38 (Brooks Flowmeter SN 8702-99252/ Model 110-W584). An oxygen feed pipe 37a connects demand regulator 37 and flowmeter 38 to conduit 18, the discharge end of pipe 37a being fitted to oxygen feed spool S in conduit 18 on the suction side of pump 30, as shown to best advantage in FIG. 5. Oxygen supply line 37b connects demand regulator 37 to a pressurized oxygen source (not shown).

It is a special feature of this invention apparatus that oxygen gas is introduced into the circulating acid solution to produce an ideal mixing action and result. Thus the gas is delivered into the center or core of the flowing solution in the direction of solution flow and in proximity to pump 30 on its suction side. Uniform distribution of the gas in the liquid phase results, the gas being in the form of small bubbles distributed through the cross section of the liquid flow from the discharge side of pump 30. The relationship of feed pipe 37a to spool S makes this desirable result possible.

The rate of flow of the recirculating liquid is controlled by regulation of the output of pump 30 by adjustment of throttling valve 39 so that the flow of the liquid approximates 18 bed volumes per minute (BVM).

Cobalt chips are charged into reactor 10 after each batch run to make up for that previously dissolved. Thus, the metal available for reaction is maintained from batch to batch at the level required for the desired level of operating efficiency.

As the dissolution reaction proceeds in normal operation, the volume of the circulating solution increases to the extent that by-product water is formed. The additional liquid volume of the system is accomodated by expansion tank 40 disposed atop reactor vessel 10 and communicating with column 10a through port 21. In normal operation expansion tank 40 will be approximately ⅔ full when the operation is terminated. Oxygen gas pressure in the system is preferably maintained during operation at about 55 psig and is limited to a maximum of 60 psig by pressure relief valve 41 fitted at the top of expansion tank 40 along with pressure gauge 42.

As indicated above, one has the option of running this Process in a manner that involves withdrawing the circulating solution at intervals and replacing it with fresh aqueous acetic acid. Thus, when the free acid content of the circulating solution falls to a predetermined level such as about 4%, valve 16 is opened and the circulating solution is drawn off and replaced with an amount of fresh acid solution approximating half the volume of that withdrawn. Oxygen gas delivery to the system is interrupted during this changeover but no metal is added.

The cobalt acetate-containing solution drawn off during a run or at the end of a run may be treated in the manner of choice for recovery of cobalt content as cobalt acetate or in other desired form.

The following illustrative, but not limiting, examples of the practice of this invention as it has been carried out under a variety of different conditions for the purpose of exploring the capabilities of the process and apparatus of this invention will afford those skilled in the art a better understanding of the various novel and important aspects of this invention:

EXAMPLE I

Using 700 gallon reactor apparatus as described above and illustrated in FIGS. 1, 4 and 5, cobalt acetate was produced in the form of an aqueous solution containing about 3% free acetic acid by subjecting cobalt metal in the form of chips of approximate size of 1¼ inch × ⅛ inch to contact initially with acetic acid solution approximating 22.3% free acid. A bed of approximately 11,000 pounds of electrolyte in a vertically disposed cylindrical reactor was subjected to contact with acid solution under initial pressure of 25 psig, oxygen flow being at the rate of 200 standard cubic feet per hour (SCFH-25° F.) at the injection point in the recirculating acid solution. Recirculating pump pressure was 75 psig and the reactor vessel initial temperature was 84° F. Pump pressure was maintained throughout the nearly 7 hours of operation in the range from 75 to 100 psig but the temperature was permitted to rise progressively to a maximum of 185° F. reached in the final hour of operation. The flow of oxygen into the recirculating solution was in the range from 200 to a maximum of 500 SCFH (at 25° to 45° F.) as necessary to maintain the oxygen level in the system for maximum metal dissolution rate. Free acid content of the circulating solution through the entire period declined at approximately constant rate to the final 3% level while the vessel oxygen gas pressure increased from initial 25 psig to final 45 psig.

The rate of dissolution in this operation was 1.1 pound cobalt per minute and approximately 660 gallons of 8% cobalt solution was produced.

EXAMPLE II

In a second run under conditions initially as set forth in Example I except that the vessel temperature was 60° F. and the pump pressure was 42 psig and the free acid content of the solution was 21.93%, the process was carried on so that the vessel temperature rose to a higher level in the early and middle stages of the run than in Example I. More importantly, the flow of oxygen gas was substantially greater throughout this second run approximating 500 SCFH at 0° F. to 550 at 38° F. while vessel oxygen gas pressure was maintained throughout at substantially lower levels than in the run of Example I (0 to 40 psig vs. 25 to 45 psig).

The rate of dissolution in this case was 1.8 pound cobalt per minute.

EXAMPLE III

In still another run like that of Examples I and II the dissolution rate was 2.3 pounds per minute. In this instance the process was operated for only 220 minutes, whereas Examples I and II were, respectively, 7 hours and 6 hours. Again, as in Example II, the oxygen gas flow rate was in the higher range (550 SCFH at 0° F. to 38° F.) during most of the run and vessel pressure was in the range of about 20 to 45 psig as in the case of Example II.

EXAMPLE IV

In this experiment the cobalt chips were loaded into the reactor to provide a bed as described in Example I and aqueous acetic acid solution of 21.36% free acid content was run through the chip bed under pump pressure from 44 to 89 psig, oxygen gas at about 40 psig being injected into the circulating solution at the rate of 370 to 550 SCFH at 20° F. The reactor vessel initial temperature was 74° F. and with a heat exchanger in use the vessel temperature rose steadily in 105 minutes to 173° F., reaching 180° F. ten minutes later, where it was maintained until the end of the 235-minute run. The leach solution at the end of the run analyzed 2.5% free acid, 9.02% cobalt and had a pH of 4.9.

EXAMPLE V

In this test of the present invention process and apparatus, equipment as described in Example I was employed and a chip bed as also described in Example I was provided. An oxygen-containing acetic acid aqueous solution was flowed through the chip bed, the solution initially having 23.3% free acid content, pH 2.9 and cobalt content of 0.44%. The total time of the run was 290 minutes starting with aqueous acid volume of 635 gallons and a cobalt chip bed charge of 593 pounds. This was the sixth in a series of runs since the addition of fresh metal had been made to the bed. The dissolution rate was measured at 2.0 pounds of cobalt per minute. Vessel temperature was as described in Example III as were oxygen input to the circulating solution and pump pressure. The expansion chamber was approximately ¾ full at the end of this run, this fill representing the progress of the dissolution reaction resulting in by-product water contribution to the total liquid volume of the system.

EXAMPLE VI

Using a smaller version of the apparatus described in Example I, the reactor itself was a pipe of 3-inch inside diameter and the recirculation loop was 1 inch inside diameter pipe served by a pump for withdrawing liquid from the bottom of the reactor and delivering it back into the reactor near its top. The reactor was initially charged with 0.15 cubic foot of cobalt chip (about 27 pounds) and 11.5 liters of acetic acid solution containing 200 grams per liter of free acid. Oxygen flow was started at the outset of the run at 40 psig input pressure, the oxygen supply, being self-regulating in response to demand as described above during the operation of the digester system. The circulation rate of the oxygen-containing acetic acid solution was maintained at 18.1 BVM i.e. approximately 19.9 gallons per minute. The rate of cobalt dissolution in pounds per hour in this run was measured as 0.48 pounds. Maximum temperature was 190° F.

EXAMPLE VII

In another test to determine the effect of recirculation solution flow rate on the rate of cobalt dissolution, the conditions of Example VI were restablished except that in this run the circulation rate of the solution was 4.5 BVM or 5.0 gallons per minute. The rate of cobalt dissolution per hour was measured over the full run at 0.21 pounds or substantially less than half the rate achieved in the run of Example VI.

As indicated above, in the course of experimentation with the present invention process and apparatus it has been found that the rate at which the acetic acid solution is flowed through the cobalt chip bed has an important bearing on the rate of cobalt metal dissolution. Since it has been demonstrated that acid content of the recirculating solution has little, if any, effect upon metal dissolution rate, the oxygen content of the solution is the critical factor in this regard. Thus at a slow flow rate, the available oxygen in the in the recirculating acid solution is depleted prior to reaching lower levels of the metal chip bed. In other words, the effective depth of the bed or the metal chip inventory is diminished to the extent that oxygen-depleted circulating acid solution flows in contact with the metal chip bed.

Figure 2:
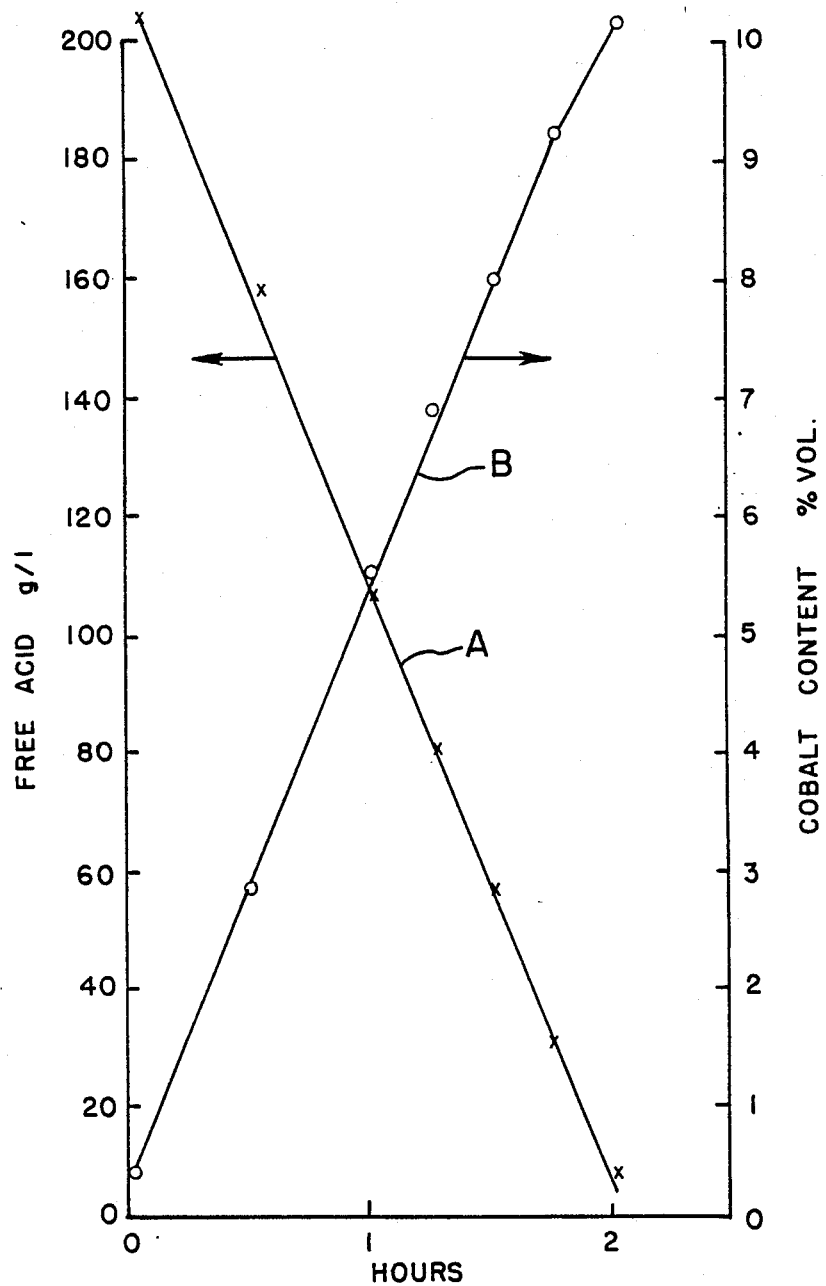
FIG. 2 is a chart on which free acid and cobalt as percent cobalt acetate in dissolution reaction solution are plotted against time in hours, the two curves representing data gathered in experimental tests of this invention process.

Referring to FIG. 2 it is apparent from Curve A and Curve B that the reaction rate is constant over the full range of free acid content of the recirculated acetic acid solution. Thus both curves illustrate the constant or straight-line relationship between free acid content over time and cobalt content of the recirculating solution over the same two-hour time interval of the experiments resulting in the data represented by Curves A and B.

Figure 3:
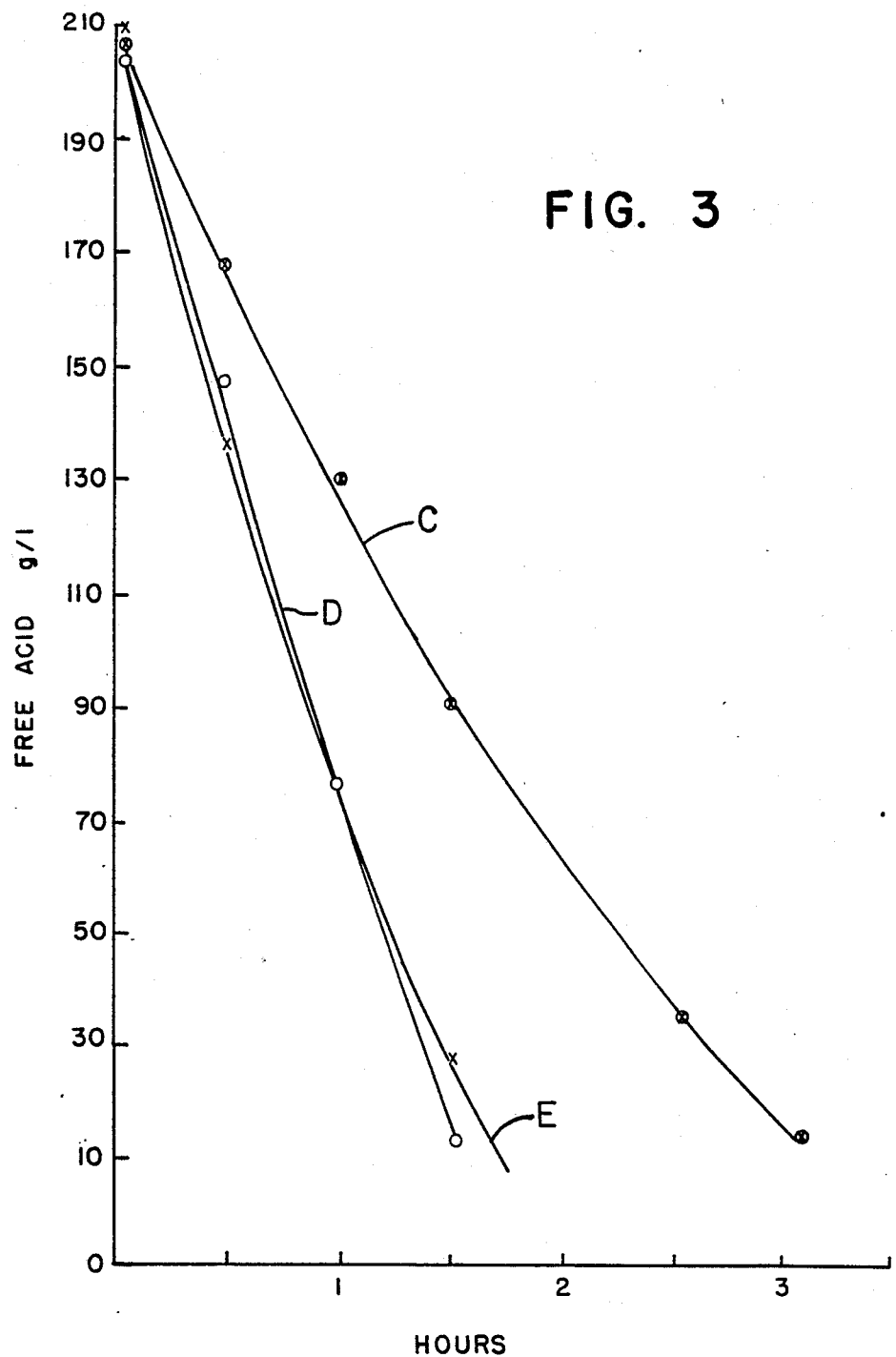
FIG. 3 is another chart on which the free acid in grams per liter is plotted against time in hours, the three curves representing data resulting from experimental runs under oxygen pressures of 20, 40 and 50 pounds per square inch gauge (psig)

Curves C, D and E of FIG. 3 illustrate the important role played by oxygen gas pressure in this process. Thus the rate of the cobalt dissolution reaction under 20 psig oxygen shown by Curve C is far less than the rate of 40 psig shown by Curve D and the rate of 50 psig of Curve E exceeds that of Curve D. The data represented by these three curves were likewise gathered in the course of experiments conducted on the apparatus of Example VI in the manner described in Example VI and under the conditions of flow rate, temperature and cobalt chip charge specified in Example VI.

Wherever in the present specification and in the appended claims percentages or proportions are recited, reference is to the weight basis unless otherwise expressly stated.

What is claimed:

1. The method of producing an aqueous cobalt acetate solution which comprises the steps of providing a bed of cobalt chips of approximate size 1¼ inch by ⅛ inch in a closed reactor vessel, establishing a circulating stream of aqueous acetic acid, introducing oxygen gas into the aqueous acid stream and thereby establishing an oxygen atmosphere in the vessel, repeatedly flowing the resulting oxygen-containing stream through the cobalt chip bed, and introducing additional oxygen gas into the circulating stream to maintain the pressure of the oxygen atmosphere between 20 and 60 pounds per square inch gauge.

2. The method of claim 1 in which the oxygen is introduced into the circulating stream to maintain the pressure of the oxygen atmosphere at about 55 pounds per square inch gauge.

* * * * *